United States Patent
Ayappa et al.

(10) Patent No.: US 12,220,530 B2
(45) Date of Patent: Feb. 11, 2025

(54) SYSTEM AND METHOD FOR AUTOMATED TITRATION OF CONTINUOUS POSITIVE AIRWAY PRESSURE USING AN OBSTRUCTION INDEX

(71) Applicant: New York University, New York, NY (US)

(72) Inventors: Indu A. Ayappa, New York, NY (US); Robert G. Norman, New Windsor, NY (US); David M. Rapoport, New York, NY (US)

(73) Assignee: NEW YORK UNIVERSITY, New York, NY (US)

( * ) Notice: Subject to any disclaimer, the term of this patent is extended or adjusted under 35 U.S.C. 154(b) by 351 days.

(21) Appl. No.: 17/654,741

(22) Filed: Mar. 14, 2022

(65) Prior Publication Data

US 2022/0409834 A1    Dec. 29, 2022

Related U.S. Application Data (63) Continuation of application No. 15/658,103, filed on Jul. 24, 2017, now abandoned, which is a continuation of application No. 12/343,972, filed on Dec. 24, 2008, now Pat. No. 9,713,688, which is a continuation of application No. 11/240,124, filed on Sep. 30, 2005, now Pat. No. 9,289,566, which is a continuation-in-part of application No. 10/862,067, filed on Jun. 4, 2004, now abandoned.

(60) Provisional application No. 60/618,969, filed on Oct. 15, 2004.

(51) Int. Cl.
*A61M 16/00*    (2006.01)
*A61M 16/04*    (2006.01)
*A61M 16/10*    (2006.01)

(52) U.S. Cl.
CPC .... *A61M 16/0051* (2013.01); *A61M 16/0069* (2014.02); *A61M 16/024* (2017.08); *A61M 16/0431* (2014.02); *A61M 16/10* (2013.01); *A61M 2016/0021* (2013.01); *A61M 2016/0027* (2013.01)

(58) Field of Classification Search
None
See application file for complete search history.

(56) References Cited

U.S. PATENT DOCUMENTS

| | | | |
|---|---|---|---|
| 5,803,066 A * | 9/1998 | Rapoport | A61M 16/0069 128/207.18 |
| 2004/0123866 A1 * | 7/2004 | Berthon-Jones | A61M 16/0006 128/204.23 |
| 2007/0161913 A1 * | 7/2007 | Farrell | A61M 16/06 600/323 |

(Continued)

*Primary Examiner* — Bradley H Philips
(74) *Attorney, Agent, or Firm* — Fay Kaplun & Marcin, LLP (57) ABSTRACT

Described is a system including an air pressure supply arrangement, a sensor and a titration device. The air pressure supply arrangement provides air pressure to a patient's airways. The sensor detects input data corresponding to a patient's breathing patterns of a plurality of breaths. The titration device receives and analyzes the input data to determine existence of breathing disorder and corresponding characteristics. The titration device generates output data for adjusting the air pressure supplied to the patient as a function of an index of abnormal respiratory events included in the input data.

14 Claims, 7 Drawing Sheets

(56) References Cited

U.S. PATENT DOCUMENTS

2008/0053440 A1* 3/2008 Farrugia ........... A61M 16/0069
128/204.23
2011/0284003 A1* 11/2011 Douglas ............... A61B 5/4836
128/204.23

* cited by examiner

FIG. 1

AIRFLOW TO AND
FROM CPAP GENERATOR

FIG. 2

AIRFLOW TO AND
FROM CPAP GENERATOR

FIG. 3

AIRFLOW TO AND
FROM CPAP GENERATOR

FIG. 4
AIRFLOW TO AND
FROM CPAP GENERATOR

FIG. 5
AIRFLOW TO AND
FROM CPAP GENERATOR

SYSTEM AND METHOD FOR AUTOMATED TITRATION OF CONTINUOUS POSITIVE AIRWAY PRESSURE USING AN OBSTRUCTION INDEX

PRIORITY CLAIM

This application is a Continuation application of U.S. patent application Ser. No. 15/658,103 filed on Jul. 24, 2017; which is a Continuation application of U.S. patent application Ser. No. 12/343,972 filed on Dec. 24, 2008, now U.S. Pat. No. 9,713,688; which is a Continuation of U.S. patent application Ser. No. 11/240,124 filed on Sep. 30, 2005, now U.S. Pat. No. 9,289,566; which is (a) a Continuation-in-part of U.S. patent application Ser. No. 10/862,067 filed on Jun. 4, 2004, now abandoned and (b) which claims priority to U.S. Provisional Patent Application Ser. No. 60/618,969 filed on Oct. 15, 2004. The entire disclosures of these patent(s)/application(s) are expressly incorporated herein by reference.

BACKGROUND

Obstructive sleep apnea/hypopnea syndrome (OSAHS) is a well recognized disorder which may affect as much as 1-5% of the adult population. OSAHS is one of the most common causes of excessive daytime somnolence. OSAHS is most frequent in obese males, and it is the single most frequent reason for referral to sleep disorder clinics.

OSAHS is associated with conditions in which there is anatomic or functional narrowing of the patient's upper airway, and is characterized by an intermittent obstruction of the upper airway during sleep. The obstruction results in a spectrum of respiratory disturbances ranging from the total absence of airflow despite continued respiratory effort (apnea), to significant obstruction with or without reduced airflow (hypopnea, episodes of elevated upper airway resistance, and snoring). Morbidity associated with the syndrome arises from hypoxemia, hypercapnia, bradycardia and sleep disruption associated with the respiratory obstructions and arousals from sleep.

The pathophysiology of OSAHS is not fully worked out. However, it is now well recognized that obstruction of the upper airway during sleep is in part due to the collapsible behavior of the supraglottic segment of the respiratory airway during the negative intraluminal pressure generated by inspiratory effort. The human upper airway during sleep behaves substantially similar to a Starling resistor which by definition limits the flow to a fixed value irrespective of the driving (inspiratory) pressure. Partial or complete airway collapse can occur associated with the loss of airway tone, which is characteristic of the onset of sleep and may be exaggerated with OSAHS.

Since 1981, positive airway pressure ("PAP") applied by a tightly fitted nasal mask worn during sleep has evolved to become the most effective treatment for this disorder, and is now the standard of care. The availability of this non-invasive form of therapy has resulted in extensive publicity for sleep apnea/hypopnea and increased appearance of large numbers of patients who previously may otherwise avoid medical treatment because of the fear of tracheostomy. Increasing the comfort of the system (e.g., by minimizing the applied nasal pressure) has been a major goal of research aimed at improving patient compliance with therapy.

PAP therapy has become the mainstay of treatment in Obstructive Sleep Disordered Breathing ("OSDB"), which includes Obstructive Sleep Apnea/Hypopnea, Upper Airway Resistance Syndrome, Snoring, exaggerated rises of sleep-induced collapsibility of the upper airway and all conditions in which inappropriate collapsing of a segment of the upper airway causes significant non-physiologic obstruction to airflow. Collapse of a portion of the airway generally occurs whenever pressure in the collapsible portion of the airway becomes sub-atmospheric. Stated another way, collapse occurs when pressure in the airway falls below a "tissue pressure" in the surrounding wall. PAP therapy is directed to maintaining pressure in the collapsible portion of the airway at or above the critical "tissue pressure" at all times. This goal is achieved by raising the airway pressure in the entire respiratory system to a level higher than this critical pressure.

Despite its success, conventional PAP systems have certain limitations. For example, the determination of the appropriate pressure for therapy, referred to as PAP titration, is normally performed in a sleep laboratory where a specific treatment pressure is determined. However, during the first week of treatment the necessary pressure to treat the OSDB may decrease, which results in a prescribed pressure that is too high and may compromise patient compliance. In addition, the patient may assume body positions or sleep stages, other than those occurring in the sleep laboratory that may change the therapeutic pressure. Finally, patients may require periodic retitration following changes in condition, such as weight gain or loss. Retitration of the PAP in the laboratory is usually expensive and is not part of the usual standard of care. Thus, there is a need for a system and method that would provide initial PAP titration and retitration to patients as required during subsequent treatments.

SUMMARY OF THE INVENTION

The present invention relates to a system including an air pressure supply arrangement, a sensor and a titration device. The air pressure supply arrangement provides air pressure to a patient's airways. The sensor detects input data corresponding to a patient's breathing patterns of a plurality of breaths. The titration device receives and analyzes the input data to determine existence of breathing disorder and corresponding characteristics. The titration device generates output data for adjusting the air pressure supplied to the patient as a function of an index of abnormal respiratory events included in the input data.

DETAILED DESCRIPTION

FIGS. 1-5 illustrate waveforms of flow from a PAP generator, obtained during the testing of a patient in sleep studies. In these tests, the patient was wearing a PAP mask connected to an air source, for example, in the manner illustrated in U.S. Pat. No. 5,065,765, the entire disclosure of which is hereby incorporated by reference. Each of these tests illustrates an epoch of 30 seconds, with the vertical lines depicting seconds during the tests. FIGS. 1-5 depict separate sweeps taken from 1 to 2 minutes apart, and with different pressures from the source of air.

Figure 1:
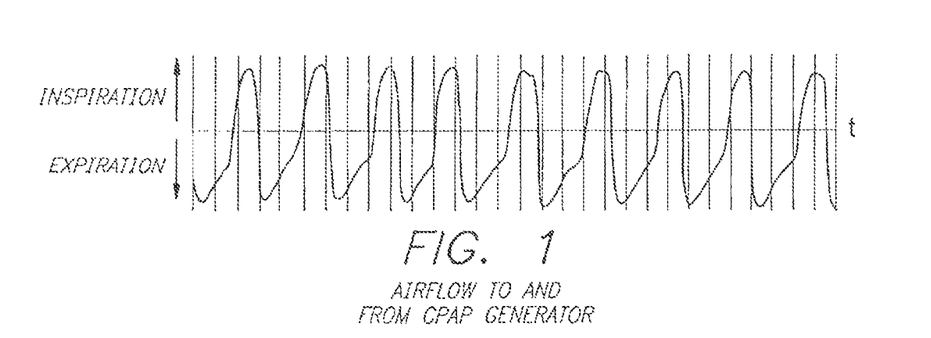
FIG. 1 shows a waveform of airflow from a sleeping patient in a 30 second epoch when subjected to a substantially constant PAP pressure of 10 cm $H_2O$.

FIG. 1 illustrates a "normal" waveform, in this instance with a Continuous Positive Airway Pressure ("CPAP") of 10 cm $H_2O$. Although this description uses a CPAP system to illustrate the system and method according to the present invention, those skilled in the art will understand that this invention is equally useful in conjunction with any variety of PAP systems supplying constant or varying pressure to patients. However, any other pressure identified as corresponding to apnea free respiration may also be used. It is noted that this waveform, at least in the inspiration periods, is substantially sinusoidal. The waveforms of FIGS. 2-5 illustrate that, as the controlled positive pressure is lowered, a predictable index of increasing collapsibility of the airway occurs, prior to the occurrence of frank apnea, periodic breathing or arousal.

Figure 2:
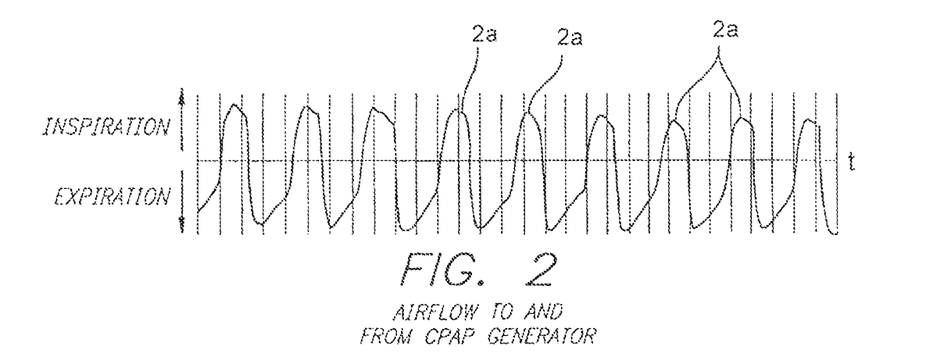
FIG. 2 shows a waveform of airflow from a sleeping patient in a 30 second epoch when subjected to a substantially constant PAP pressure of 8 cm $H_2O$.
Figure 3:
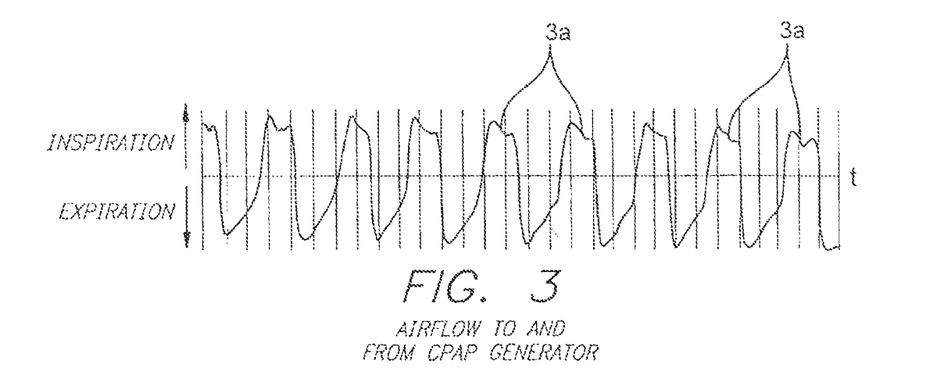
FIG. 3 shows a waveform of airflow from a sleeping patient in a 30 second epoch when subjected to a substantially constant PAP pressure of 6 cm $H_2O$.
Figure 4:
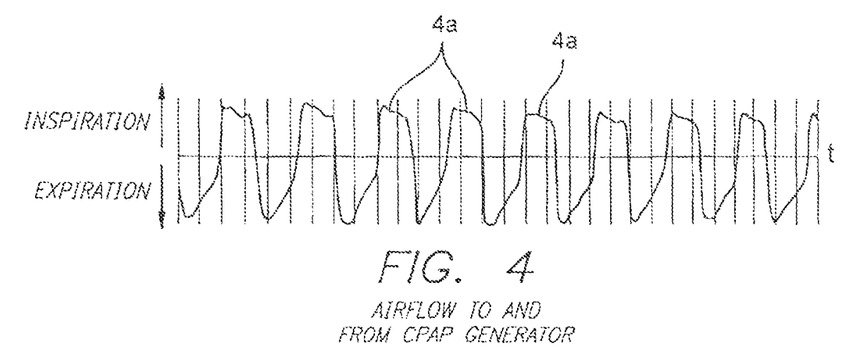
FIG. 4 shows a waveform of airflow from a sleeping patient in a 30 second epoch when subjected to a substantially constant PAP pressure of 4 cm $H_2O$.
Figure 5:
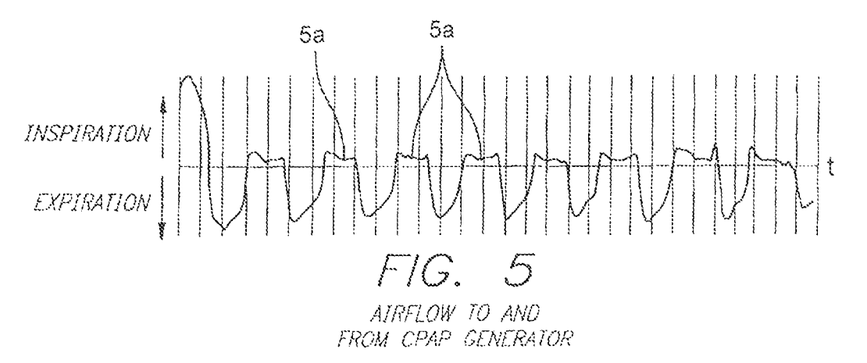
FIG. 5 shows a waveform of airflow from a sleeping patient in a 30 second epoch when subjected to a substantially constant PAP pressure of 2 cm $H_2O$.

When CPAP pressure is decreased to 8 cm $H_2O$, as illustrated in FIG. 2, a partial flattening of the inspiratory flow waveform, at region 2a, begins. This flattening becomes more definite when the controlled positive pressure is decreased to 6 cm $H_2O$, as seen in the region 3a of FIG. 3. The flattening becomes even more pronounced, as seen in the region 4a of FIG. 4, when the controlled positive pressure is reduced to 4 cm $H_2O$. These reductions in the CPAP pressure from the pressure of apnea free respiration, result in, for example, snoring or other signs of patient airway obstruction. When the CPAP pressure is further reduced to 2 cm $H_2O$, as illustrated in FIG. 5, inspiratory flow may decrease to a virtually zero level during inspiratory effort, as seen in the region 5a. Shortly after the recording of the waveform of FIG. 5, the patient in the example developed frank apnea and awoke.

Figure 6:
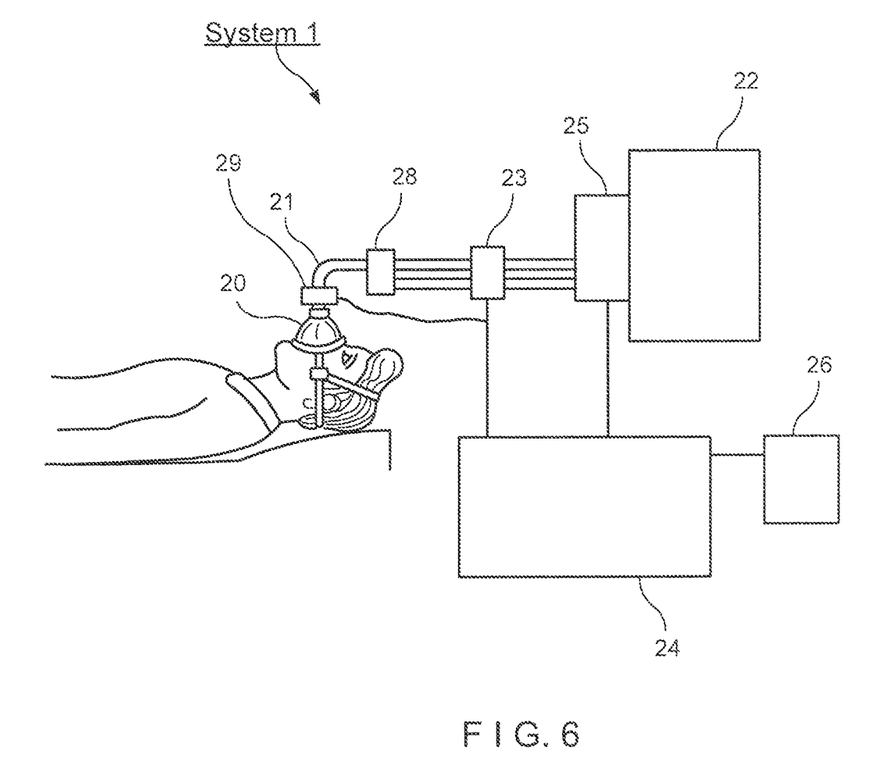
FIG. 6 shows an exemplary embodiment of a system according to the present invention.

FIG. 6 shows an exemplary embodiment of a system 1 according to the present invention. The system 1 may include a mask 20 that is connected via a tube 21 to receive airflow at a particular pressure from a flow generator 22 or any other suitable airway pressure supply system. The amount of pressure provided to a particular patient varies depending on that patient's particular condition.

The mask 20 may cover the patient's nose and/or mouth. However in other exemplary embodiments according to the present invention, the mask 20 is a nasal cannula. Conventional flow and/or pressure sensors 23 are coupled to the tube 21 to detect the volume of the airflow to and from the patient and the pressure supplied to the patient by the generator 22. The sensors 23 may be internal or external to the generator 22. Signals corresponding to the airflow and the pressure from the sensors 23 are provided to a processing arrangement 24. The processing arrangement 24 generates pressure control outputs signals to a conventional flow control device 25 that controls the pressure applied to the flow tube 21 by the flow generator 22. Those skilled in the art will understand that, for certain types of flow generators which may be employed as the flow generator 22, the processing arrangement 24 may directly control the flow generator 22, instead of controlling airflow therefrom by manipulating a separate flow control device 25.

The system 1 may also include a venting arrangement 28 which allows for gases exhaled by the patient to be diverted from the incoming air to prevent re-breathing of the exhaled gases. In an alternative exemplary embodiment of the present invention, the system 1 may include a further sensor 29 situated at or near the mask 20. The further sensor 29 is connected to the processing arrangement 24 and provides data regarding the airflow and the pressure in the mask 20 to the processing arrangement 24.

Those skilled in the art will understand that the system 1 may be utilized for the purpose of detecting abnormal respirations and flow limitations in the patient's airway. Alternatively, the system 1 may be utilized for detection of sleeping disorders (e.g., flow limitations), autotitration and treatment of such sleeping disorders.

The system 1 also includes an automatic titration device 26 which provides an initial titration (i.e., determination of an appropriate pressure or an appropriate varying pressure function for a particular patient) as well as subsequent retitrations. The titration device 26 may be a portable device which is attachable (e.g., using convention wired or wireless techniques) to the processing arrangement 24 when it is necessary to obtain appropriate pressure for the PAP therapy or to update previously calculated pressures. Those skilled in the art will understand that the titration device 26 may be attached to any conventional PAP therapy system. Alternatively, the titration device 26 may be built into the system 1 (e.g., the titration device 26 may be combined with the processing arrangement 24).

Figure 7:
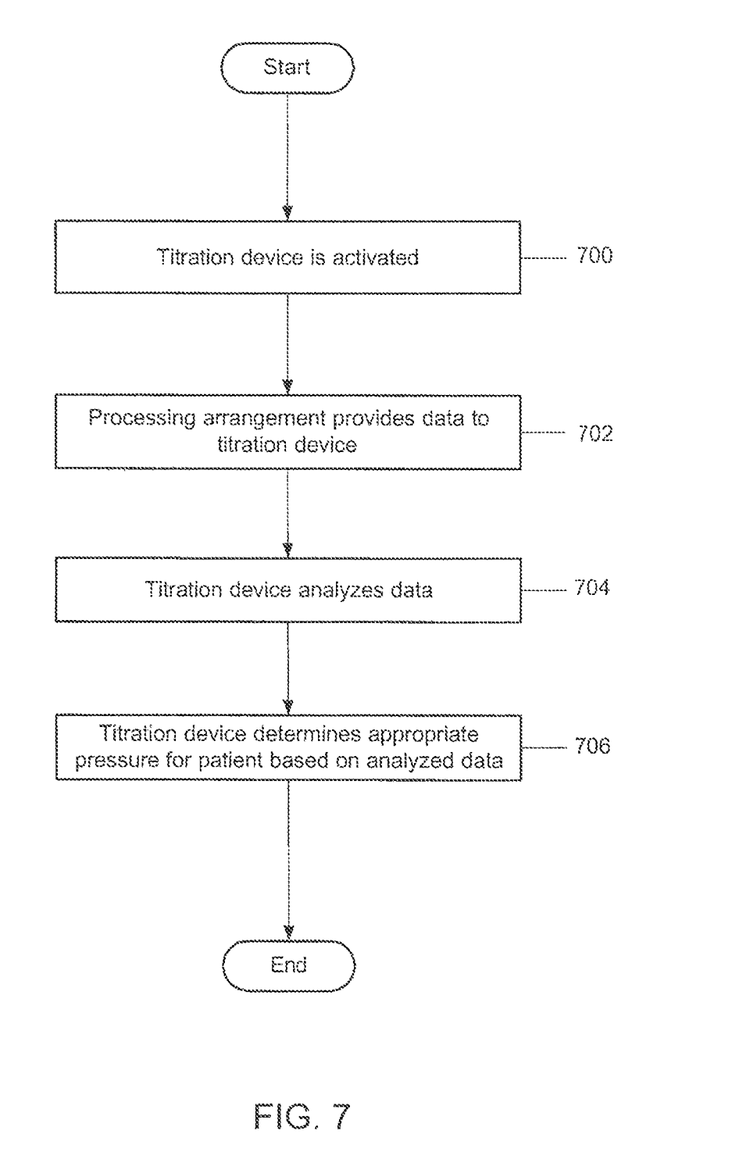
FIG. 7 shows an exemplary embodiment of a method according to the present invention.

FIG. 7 shows an exemplary method according to the invention for automatic titration to determine an appropriate pressure or varying pressure function for the PAP therapy. In step 700, the titration device 26 is activated, e.g., (a) by powering the titration device 26 if it is a part of the processing arrangement 24 or (b) by connecting the titration device 26, if it is a stand-alone unit, to the processing arrangement 24. Since it may not be necessary to perform titration on a daily basis, the titration device 26 may be activated by the patient or medical personnel initially to obtain appropriate data for calculation of the pressure or pressure function for the PAP therapy. The titration device 26 can be again activated at such times as may be determined are desired to retitrate to ensure the PAP therapy is properly tailored to the patient's current condition. The activation process may be performed immediately prior to initiation of the PAP therapy or may be preset to automatically activate at predetermined points, such as days and/or times.

Once activated, the titration device 26 may remain active for a predetermined period of time. For example, the titration device 26 may remain active for a specific period of time (e.g., a single sleeping cycle of 6-8 hours) or until it is manually deactivated. While active, the titration device 26 may work in the background processing and analyzing data collected by the processing arrangement 24 (step 702) without interfering with the PAP therapy. In particular, the processing arrangement 24 transmits data to the titration device 26 data which includes, among other information, the patient's airflow and the pressure applied to the airways of the patient. Such data may be provided continuously or periodically (e.g., every hour). Alternatively, the titration device 26 may be programmed to update immediately the PAP treatment under predetermined conditions.

The data collected by the titration device 26 may be stored in a database with, for example, data related to each particular patient collected during various titration procedures. Or, collected data may be stored together so that the data from several titration procedures may be accessed and analyzed by the titration device 26 to determine appropriate pressure controls for that patient. For example, the data may be stored on a removable memory arrangement which may be kept by the patient and provided to the titration device 26 each time the titration procedure for this patient is initiated. Alternatively, data for multiple patients may be stored in corresponding files of a single memory arrangement. Those skilled in the art would understand that the single memory arrangement may be a part of the system 1; alternatively, the single memory arrangement may be situated at a remote location that can be accessed via a communications network (e.g., the Internet, VPN, etc.).

In step 704, the titration device 26 analyzes the collected data. In particular, data relating to patient airflow is utilized to accurately map patient's breathing patterns. The titration device 26 analyzes these breathing patterns to detect abnormal respiratory events and to identify the conditions under which they arise. Abnormal respiratory events that may be identified include apnea, hypopnea and events of elevated upper airway resistance. Apnea is identified by a cessation of respiratory airflow in the patient, where the cessation can last, for example, approximately ten seconds. Hypopnea is identified by a decrease in amplitude of the airflow signal relative to a baseline value, where the decrease can last, for example, approximately ten seconds. Elevations in the resistance of the upper airway may be identified by changes in the shape of the inspiratory airflow contour. The airflow signal from the entire collection period may be analyzed for the presence of sleep disordered breathing events.

In step 706, based on the analysis of respiratory events, the titration device 26 determines, using a predefined algorithm, an appropriate pressure or a varying pressure function to be supplied to the patient. The counts and other indexes of respiratory events (e.g., a total time of abnormal respiration, a percentage of abnormal breath, total number of events in general and by type, etc.) that occurred during the previous collection period indicate the efficacy of the pressure administered. When the count or index increases to beyond a preset absolute value or relative value (e.g., compared to previous values for that patient) the pressure may be increased for the next CPAP period. If the number of events is below a preset value then the pressure may be decreased for the next predefined time period. In addition, the response to previous pressure decreases may also be incorporated into the pressure determination algorithm. For example, the titration device 26 may determine that a constant pressure supplied to the patient needs to be increased if a number of abnormal events identified reaches a threshold within a specified time period (e.g., when number of apneas, hypopneas or elevated resistance events exceeds the preset limit or increases by a specified amount above the previous values for the patient).

Alternatively, the supplied pressure may need to be decreased or remain unchanged if no abnormal respiratory events are detected or if the number detected is less than the threshold level. If the titration device 26 is used to adjust a variable pressure supplied to a patient, those skilled in the art will understand that, based on the number of abnormal events identified and the circumstances under which they occurred, any number of modifications of the pressure supply function may be initiated. For example, if a pressure supplied to the patient varies substantially sinusoidally, an average value or an amplitude of the pressure may be adjusted.

In a preferred embodiment of the present invention, the titration device 26 determines the appropriate pressure or a varying pressure function to be supplied to the patient using a unique obstruction index ("OI"). Embodiments of the OI according to the present invention combine several indices of elevated resistance, such as snoring and flow limitation ("FL"), into one number. One embodiment of the OI includes the sum of the apnea/hypopnea index ("AHI"), the number of discrete (e.g., 10-120 seconds) FL events per hour, and an amount of time in sustained (e.g., greater than 2 minutes) FL.

The validity the OI was evaluated in a study of 4 patients previously diagnosed with OSAHS. The patients were monitored in their homes for multiple nights (mean 19 nights, range 10-32 nights) at different levels of CPAP, while pressure and airflow were continuously monitored. Changes in collapsibility were produced in patients with OSAHS by varying an applied nasal CPAP. CPAP was varied 1-3 cm $H_2O$ above and below the patient's prescription pressure as previously obtained from an in-lab titration. Several indices of obstructive SDB were calculated including: a traditional AHI, the OI (as described above), and a respiratory disturbance index ("RDI").

The AHI was calculated as the sum of apneas and hypopneas per hour and was based on airflow amplitude changes >50%. The OI was calculated as the sum of all obstructive events <2 mins+⅓ of the time spent with breaths showing abnormal morphology of flow (e.g., time spent in sustained FL). The abnormality (flow limitation) was associated with a high upper airway collapsibility (resistance). The justification for the factor of ⅓ was that when this formula for calculating OI is applied to a normal subject with minimal AHI and with sustained flow limitation only, the OI value had to be below 15. As one of ordinary skill in the art will understand however, the factor may be adjusted up or down to reflect additional received data.

Figure 8:
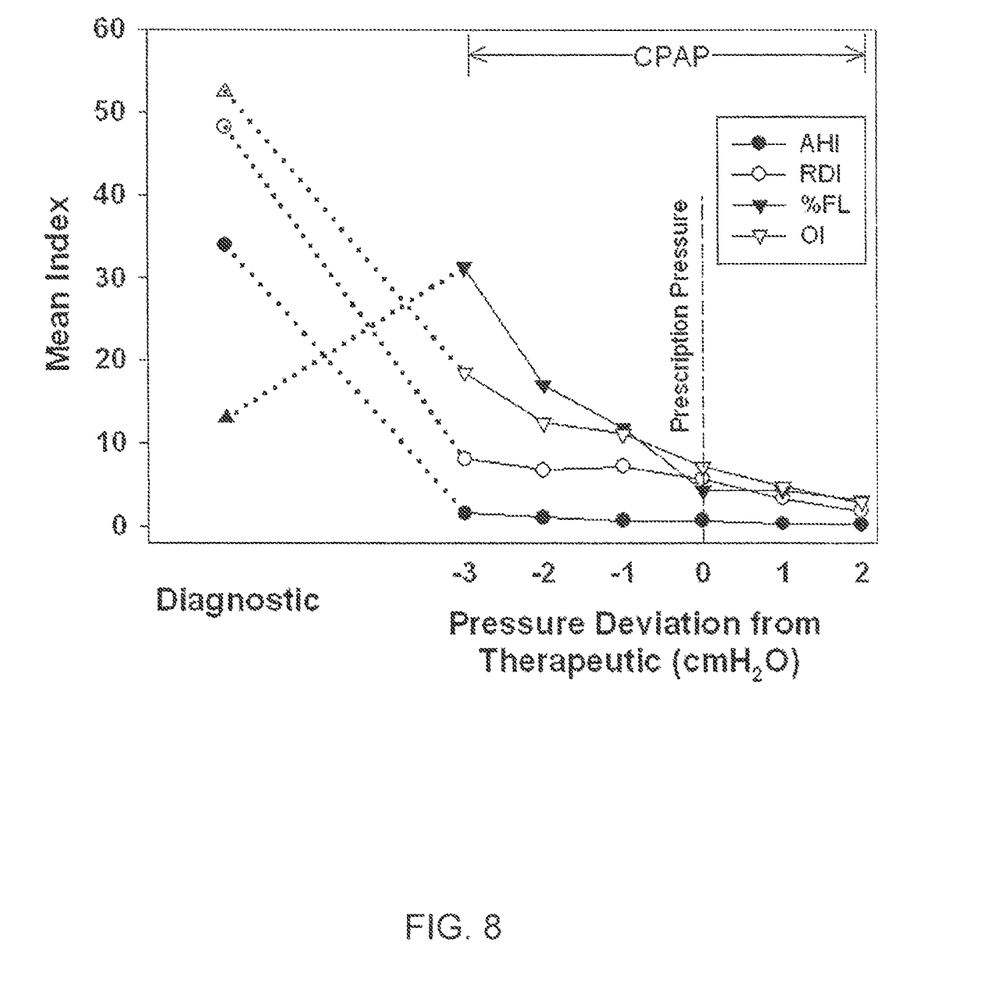
FIG. 8 shows graphically indices of obstruction sleep disordered breathing as a function of pressure deviation from a therapeutic pressure.

FIG. 8 shows graphically each calculated index as a function of pressure deviation from the therapeutic pressure. As shown, all indices were low above the prescription pressure. However, up to 3 cm below this pressure, AHI remained flat. RDI rose above 5 but did not vary with CPAP. In contrast, both sustained FL and OI increased sharply below therapeutic pressure and are inversely related to CPAP. The present analysis assumes a difference between therapeutic and subtherapeutic CPAP exists. The study showed that the OI according to the present invention can detect changes in the pattern of SDB that are produced by increased levels of the collapsibility and upper airway resistance (by lowering CPAP) that are masked when the AHI alone is used. AHI and RDI are not as sensitive to these differences as the OI and sustained FL. Although the sustained FL % works well in this range of pressures, it can fall markedly whenever the AHI is elevated (as in the diagnostic night) and thus the OI has a conceptual advantage.

Figure 9A:
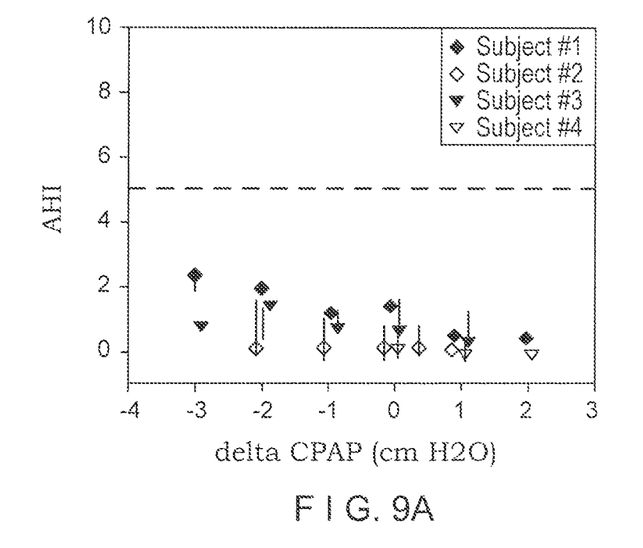
FIG. 9A shows graphically an apnea/hypopnea index at different CPAP levels.
Figure 9B:
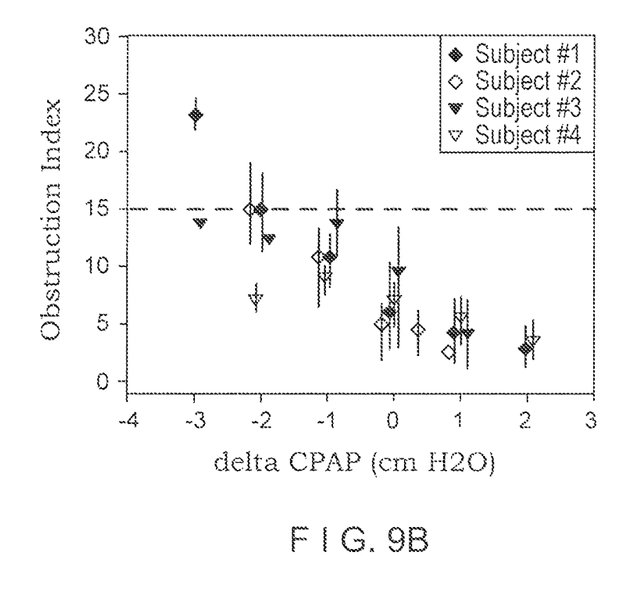
FIG. 9B shows graphically an obstruction index according to the present invention at different continuous positive airway pressure levels.

FIGS. 9A and 9B show variability in the AHI and OI, respectively, at different CPAP levels. The difference between the actual pressure delivered and the prescribed CPAP pressure is plotted on the x-axis (delta CPAP) against the AHI or the OI on the y-axes wherein each symbol represents one subject. The mean value of each index over multiple nights of recording at that pressure along with the range at that pressure is plotted. Note that the AHI was <5 per hour at all pressures on all nights, which would have been considered therapeutic. The OI shows significant variability at pressures below the patients prescribed therapeutic pressure and captures the changes in sleep disordered breathing at sub-therapeutic pressures.

Current clinical definitions for adequacy of CPAP or other therapeutic modalities generally use an AHI values less than 5/hour as optimal. The disclosed data suggests that use of this cutoff could result is significant residual obstruction as seen in the OI, and could potentially contribute to residual sleepiness in subjects who are thought to be on therapeutic levels of CPAP based on their AHI.

In the disclosed study, pilot data was obtained in subjects with OSAHS (n=9) who underwent psychomotor vigilance task ("PVT") testing following a night of nocturnal polysomnography ("NPSG") in a lab. NPSG data was also obtained in 5 normal volunteers/snorers, without PVT. Subjective sleepiness measures (e.g., an Epworth Sleepiness Scale or "ESS") were obtained in all subjects and an OI was calculated as described above.

Figure 10:
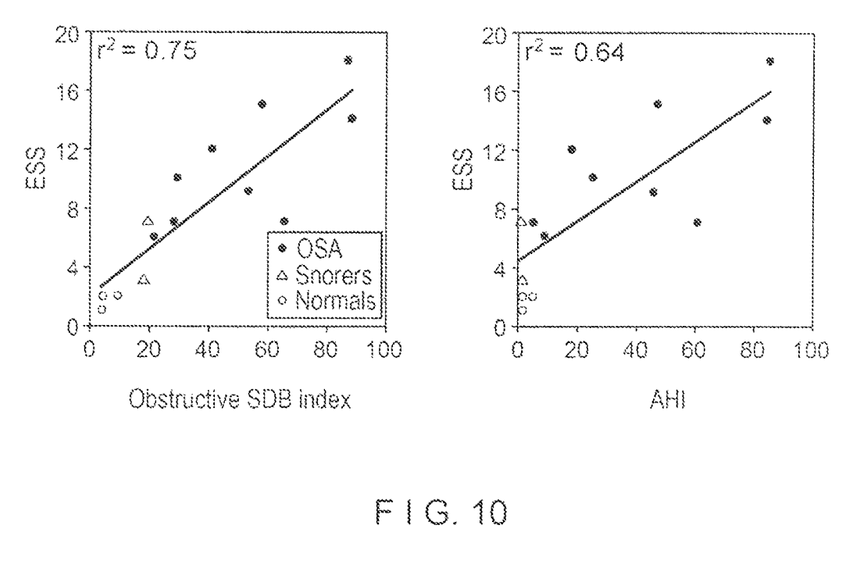
FIG. 10 shows graphically a correlation between a subjective sleepiness measure and an obstruction index according to the present invention and a correlation between an apnea/hypopnea index and an obstruction index according to the present invention.
Figure 11:
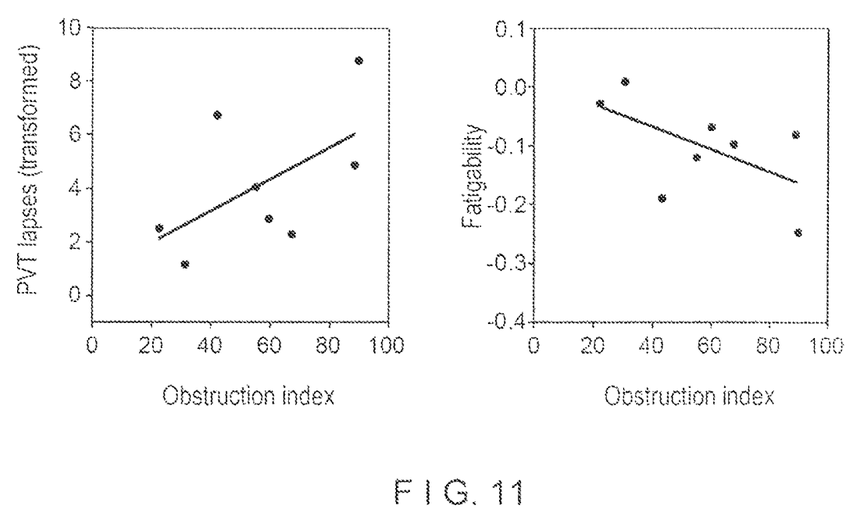
FIG. 11 shows graphically a correlation between psychomotor vigilance task lapses and an obstruction index according to the present invention and a correlation between a fatiguability and an obstruction index according to the present invention.

FIG. 10 shows that a good relationship between the ESS and the OI was obtained in all subjects ($r^2$=0.75). The relationship of ESS to AHI was also good in this small group ($r^2$=0.64), however there is no variability in AHI values closer to zero. The PVT data obtained in the patients shows a good correlation between the obstructive SDB index and the PVT lapses (transformed) and fatigability. Thus, the OI correlates to outcomes of subjective sleepiness (ESS) and objective daytime function measured by the PVT.

As described in reference to the disclosed study, the titration device 26 of the system 1 may analyze data collected during, e.g., a predetermined time period. For example, the predetermined time period may be a single sleeping cycle such as one night of observation. Alternatively, or in addition, the predetermined time period may be a portion of the single sleeping cycle such as one or two hours of observation. The pressure may be adjusted for the subsequent time period. For example, the pressure may be adjusted once per hour in response to events occurring during the previous hour.

The titration process may then be repeated during the subsequent time period using the adjusted pressure to evaluate the efficacy of the adjusted pressure. Thus, over a several time periods, the titration process may be repeated to enhance the accuracy with which the appropriate pressure is determined. In an alternative embodiment, the titration device 26 may be adapted to continually collect data for the entire duration of the treatment so that the titration process is continuously updated.

As described above, the titration device 26 according to the present invention may be manufactured as a portable stand-alone unit. Such a unit may be easily attached to most conventional therapy systems by positioning the device in the flow path, parallel to the patient and the flow generator 22. If the generator 22 were externally controllable (e.g., by a serial interface), then the titration device 26 may be connected to an external control. Alternatively, a variable pressure valve could be incorporated into the stand-alone unit to control the pressure directly. The valve can mitigate the cost of a therapy system since the patient may rent the titration device 26 only when titration is necessary.

The system 1 may determine appropriate pressures by adjusting pressure only at the beginning of a sleeping cycle and by operating over the course of several sleeping cycles to arrive at a more accurate image of the patient's breathing patterns. For example, some patients may have "good" or "bad" nights which may not be representative of an "average" night for the patient. In contrast, conventional automatic titrating systems may generate immediate feedback responses to the abnormal respiratory events from which they attempt to determine a single therapeutic pressure. Conventional titration systems generally obtain data only during a single sleeping cycle, since multiple visits to sleep clinics, where these systems are located, are unlikely. Furthermore, the more accurate the pressure supplied to a particular patient, the more likely the patient will regularly make use of this PAP therapy.

Another advantage of the present invention is that it may also be used in ongoing treatment of OSDB patients with varying pressure needs. In these cases, the titration device 26 is connected to the PAP therapy system continually so that the pressure supplied may be constantly adjusted by retitration.

In the preceding description, the present invention has been described with reference to specific exemplary embodiments thereof. It will, however, be evident that various modifications and changes may be made thereunto without departing from the broadest spirit and scope of the present invention.

What is claimed is:

1. A device for supplying air to a patient in need of positive airway pressure (PAP) comprising:
   an air supplier configured to administer a PAP flow to the patient's airways; and
   a controller configured to continuously adjust a pressure of the PAP flow as a function of an obstruction index of different abnormal respiratory events in breathing patterns of the patient,
   wherein the index includes at least one of (i) an apnea/hypopnea index (AHI), (ii) a number of discrete flow limitation events per hour, and (iii) an amount of time in sustained flow limitation and
   wherein the obstruction index includes a sum of (i) the AHI, (ii) the number of discrete flow limitation events per hour, and (iii) the amount of time in sustained flow limitation.

2. The device of claim 1, wherein the abnormal respiratory events include at least one of an apnea, a hypopnea, an event of upper airway resistance, snoring and a flow limitation.

3. The device of claim 1, wherein the obstruction index includes a sum of the different abnormal respiratory events.

4. The device of claim 1, wherein the obstruction index includes a sum of a plurality of indices of elevated resistance.

5. The device of claim 1, wherein the different abnormal respiratory events in the breathing patterns are temporally separated from one another.

6. The device of claim 1, wherein when the obstruction index is lower than a predefined value, the pressure of the PAP flow is decreased, and when the obstruction index is greater than the predefined value, the pressure of the PAP flow is increased.

7. The device of claim 1, wherein the patient has obstructive sleep apnea/hypopnea syndrome (OSAHS).

8. The device of claim 1, wherein the controller is configured to receive input data corresponding to an airflow of the patient from one or more sensors and analyze the input data to determine the patient's breathing patterns.

9. A method for treating a patient with obstructive sleep apnea/hypopnea syndrome (OSAHS), comprising:
   administering a PAP flow from an air supplier to airways of the patient; and
   continuously adjusting, by a controller, a pressure of the PAP flow as a function of an obstruction index of different abnormal respiratory events in breathing patterns of the patient,
   wherein the obstruction index includes at least one of (i) an apnea/hypopnea index (AHI), (ii) a number of discrete flow limitation events per hour, and (iii) an amount of time in sustained flow limitation and wherein the obstruction index includes a sum of (i) the AHI, (ii) the number of discrete flow limitation events per hour, and (iii) the amount of time in sustained flow limitation.

10. The method of claim 9, wherein the abnormal respiratory events include at least one of an apnea, a hypopnea, an event of upper airway resistance, snoring and a flow limitation.

11. The method of claim 9, wherein the obstruction index includes a sum of the different abnormal respiratory events.

12. The method of claim 9, wherein the obstruction index includes a sum of a plurality of indices of elevated resistance.

13. The method of claim 9, wherein when the obstruction index is lower than a predefined value, the pressure of the PAP flow is decreased, and when the obstruction index is greater than the predefined value, the pressure of the PAP flow is increased.

14. The method of claim 9, wherein the different abnormal respiratory events in the patient's breathing patterns are temporally separated from one another.

* * * * *